United States Patent [19]

Kaplan et al.

[11] 4,400,394
[45] Aug. 23, 1983

[54] BENZYLIDENE DERIVATIVES

[75] Inventors: Jean-Pierre Kaplan, Plessis; Naurice Jalfre, Paris; Don P. Giudicelli, Fontenay sous Bois, all of France

[73] Assignee: Synthelabo, Paris, France

[21] Appl. No.: 289,148

[22] Filed: Aug. 3, 1981

Related U.S. Application Data

[63] Continuation of Ser. No. 107,512, Dec. 27, 1979, abandoned.

[30] Foreign Application Priority Data

Aug. 1, 1975 [FR] France ............... 75 24065

[51] Int. Cl.³ ............ C07C 101/30; A61K 31/195
[52] U.S. Cl. ................. 424/319; 424/309; 424/324; 560/35; 562/440; 564/171; 564/174
[58] Field of Search ............. 562/440; 424/419

[56] References Cited

U.S. PATENT DOCUMENTS 3,966,793 6/1976 Schmitt .................. 560/35
4,089,875 5/1978 Jaunin .................. 560/35

FOREIGN PATENT DOCUMENTS 2282270 3/1976 France .

OTHER PUBLICATIONS

Al-Sayyab et al., J. Chem. Soc(c), pp. 406-410 (1968).
Hope et al., Tet. Letters, #22, pp. 2261-2264 (1972).
Wilson et al., "Org. Medicinal & Pharmaceutical Chem.", J. B. Lippincott Co., pp. 39, 40 & 50 (1954).

Primary Examiner—James H. Reamer
Attorney, Agent, or Firm—Wegner & Bretschneider

[57] ABSTRACT

Compounds of the formula:

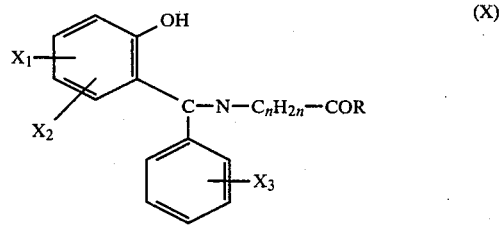

in which $X_1$, $X_2$ and $X_3$, which are identical or different, each represent hydrogen, halogen, methyl, or methoxy, n represents an integer from 1 to 10, and R represents hydroxyl, OM, $NH_2$, $NH(CH_2)_3$—COOH, —$NH(CH_2)_3$—COOM, (where M represents an alkali metal atom), $NH(CH_2)_3$—$COOC_2H_5$, NH-cycloalkyl, NH-phenyl, NH-benzyl (where the benzyl radical is unsubstituted or substituted by halogen or trifluoromethyl), NH-alkyl, N(alkyl)$_2$ and N-(alkyl)-(benzyl), the aforesaid alkyls being straight or branched and having from 1 to 4 carbon atoms and the aforesaid cycloalkyls having from 3 to 6 carbon atoms, except that when $X_1$ and $X_3$ are both hydrogen, n is 1 and R is OH, $X_2$ is not chlorine in the 5-position are useful in the treatment of epilepsy by oral or parenteral administration.

14 Claims, No Drawings

BENZYLIDENE DERIVATIVES

This application is a continuation of application Ser. No. 107,512 filed Dec. 27, 1979 now abandoned.

γ-Aminobutyric acid (GABA) is considered to act on the central nervous system as an inhibitor of neurotransmission. (See "GABA in nervous system transmission", Roberts E., Chase T. W., and Tower D. B., Raven Press 1976). Some authors (ibid., and "Epilepsy and γ-aminobutyric acid-mediated inhibition", Meldrum B. S., Int. Rev. Neurobiol, 12, Academic Press 1975) have shown that compounds capable of increasing the cerebral concentration of GABA by blocking its ensymatic degradation possess antiepileptic activity. GABA itself has been used with success in some cases of epilepsy (Roberts et al. loc. cit. pages 461–478). However the fact that very large quantities of GABA need to be administered to obtain the desired therapueutic effect and the fact that GABA does not easily cross the blood-brain barrier and does not therefore penetrate the central nervous system after oral or parenteral administration (Van Gelder N. M., J. of Neurochem., 12, pp 239–244, 1965), suggest that an antiepileptic effect following the administration of GABA is connected with a mechanism in which GABA does not act as an inhibitor of central nervous transmission. Further, the administration of GABA leads to substantial sideeffects (hypotension, bradycardia, and sedation).

The applicants have synthesised a family of new products which can be considered as possessing a "GABA-mipetic" activity; these compounds are capable of penetrating directly into the brain, providing it with the defence mechanism necessary to prevent or cure epileptic crises, when they are administered by the usual routes (oral, endo-rectal or parenteral).

The present invention thus provides the α-phenylbenzylidene derivatives of the general formula:

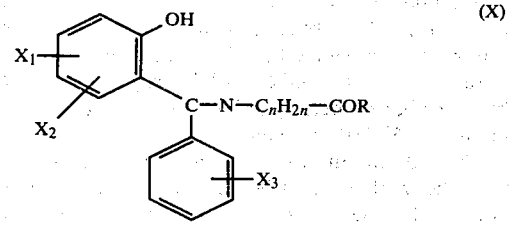
(X)

in which $X_1$, $X_2$ and $X_3$, which are identical or different, each represent, independently of one another, a hydrogen or halogen atom, especially chlorine or fluorine, or a methyl or methoxy radical, n represents an integer from 1 to 10, and R represents hydroxyl, OM, $NH_2$, $NH(CH_2)_3$—COOH, —$NH(CH_2)_3$—COOM, (where M represents an alkali metal atom, in particular sodium), $NH(CH_2)_3$—$COOC_2N_5$, NH-cycloalkyl, NH-phenyl, NH-bensyl (where the benzyl radical is unsubstituted or substituted by halogen or/and trifluoromethyl), NH—alkyl, N—(alkyl)$_2$ and N—(alkyl)-(benzyl), the aforesaid alkyls being straight or branched and having from 1 to 4 carbon atoms and the aforesaid cycloalkyls having from 3 to 6 carbon atoms, except that when $X_1$ and $X_3$ are both hydrogen n is 1 and R is OH, $X_2$ is not chlorine in the 5-position.

The compounds of the invention can be used in human and veterinary therapy, especially as antiepileptic agents, because of their activity on the cerebral metabolism.

They can be prepared by application of known methods, and in particular by the following reaction:

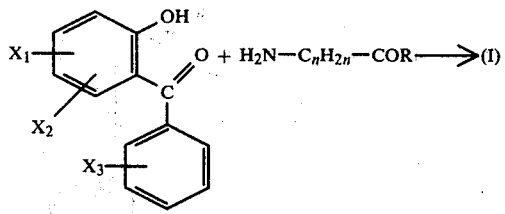

wherein the symbols have the same meaning as in the formula (I).

This reaction is advantageously carried out in a polar solvent, such as an alcohol or a glycol, in particular methanol or ethanol which can contain a little water, at a temperature between 10° C. and the boiling point or the solvent, and in the presence of an alkali metal, an alkali metal alcoholate or an alkali metal hydroxide or a quaternary hydroxy-ammonium hydroxide such as Triton B.

The amides can also be prepared from the corresponding acid by reaction between the acid

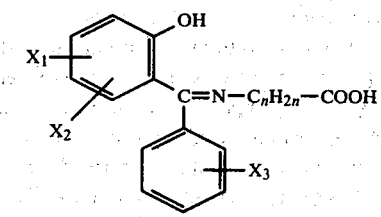

and the corresponding amine RN in the presence of carbonyl-diimidanole:

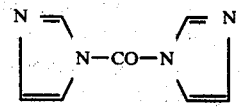

The benzophenone starting materials may be prepared from the corresponding benzoic acids in accordance with the following reaction scheme:

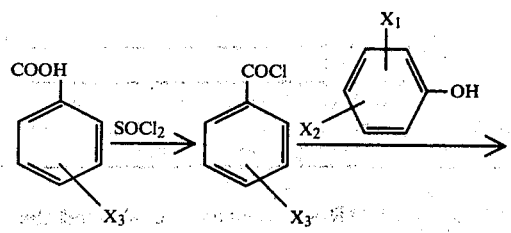

-continued

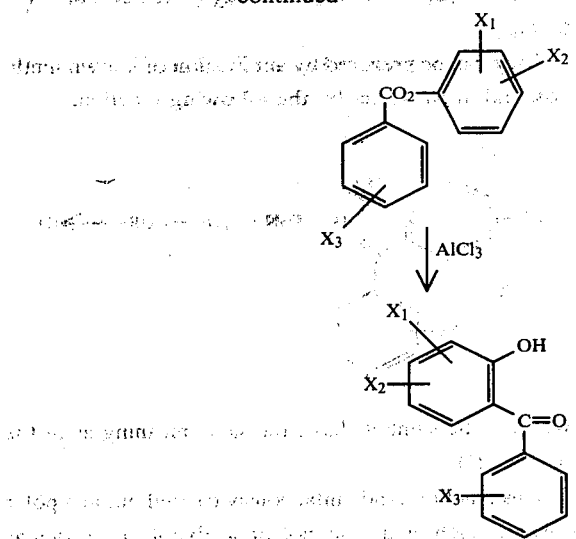

The non-limiting Examples which follow illustrate how the invention may be carried out. Temperatures are in degrees C.

EXAMPLE 1

Sodium 4-N-(α-phenyl-5-fluoro-2-hydroxy-benzylidenyl)-amino-butyrate [(I): $X_1=5$-F, $X_2=X_3=$H, $n=3$, $R=$CNa: code number: SL-D.010]

5 g of 4-aminobutyric acid and 11.5 g of 2-hydroxy-5-fluoro-benzophenone are dissolved in 500 ml of ethanol and 10 ml of 5.3 N sodium methylate are added. A limpid solution is obtained, which is evaporated under reduced pressure. The residue is dissolved in water and 4-N-(α-phenyl-5-fluoro-2-hydroxy-benzylidenyl)-amino-butyric acid is precipitated, in the form of an oil, by adding 0.1 N citric acid until the pH is 4. This acid is purified by dissolving it in alcohol, evaporating the solution and crystallising the residue from petroleum ether. 10.2 g of the acid yield=70%) are collected. The acid melts at 101°.

This acid is converted to its sodium salt in the following manner. 10.3 ml of a 3.14 N sodium methylate solution are added to 9.8 g of acid dissolved in 500 ml of absolute ethanol. The solution obtained is evaporated to dryness and the residue is filtered on a glass frit, onto which it is washed with ether. It is suction-drained, and dried in a vacuum desiccator. 10.3 g (yield=98%) of sodium 4-N-(α-phenyl-5-fluoro-2-hydroxy-benzylidenyl)-amino-butyrate, decomposing substantially at 250°, are thus obtained.

| Analysis: | | | | |
|---|---|---|---|---|
| Calculated %: | C 63.16 | H 4.68 | N 4.33 | Na 7.11 |
| Found %: | 63.09 | 4.67 | 4.28 | 7.14 |
| | 63.06 | 4.65 | 4.33 | — |

The IR and the NMR spectra have confirmed the structure of the compound.

EXAMPLE 2

Sodium 4-N-[α-(3-fluorophenyl)-5-fluoro-2-hydroxy-benzylidenyl]-amino-butyrate [(I): $X_1=5$-F, $X_2=$M, $X_3=3$-F, R=ONa, $n=3$; code number: SL-D.044].

The following are obtained successively by a method entirely similar to that described in Example 1:
4-N-[α-(3-Fluorophenyl)-5-fluoro-2-hydroxy-benzylidenyl]-amino-butyric acid, in a yield of 42.2%, melting point=84.5°–85.5°, and the corresponding sodium salt, in a yield of 85.3%; melting point=202° (decomposition).

| Analysis: | | | | | |
|---|---|---|---|---|---|
| Calc % (with 1.08% of water): | C 59.18 | H 4.21 | N 4.06 | F 11.00 | Na 6.67 |
| Found %: | 59.26 | 4.32 | 3.96 | 10.67 | 6.80 |
| | 59.24 | 4.32 | 3.91 | 10.75 | — |

The IR and NMR spectra have confirmed the structure of the compound.

EXAMPLE 3

Sodium 4-N-[α-(4-fluorophenyl)-5-fluoro-2-hydroxy-benzylidenyl]-amino-butyrate [(I): $X_1=5$-F, $X_2=$H, $X_3=4$-F, $n=3$, R=ONa: code number SL-D.045]

5.2 g (0.0505 mol) of 4-aminobutyric acid, 2.0 g (0.0505 mol) of powdered sodium hydroxide and 12 g (0.0512 mol) of 5,4'-difluoro-2-hydroxy-benzophenone are introduced into a 500 ml flask. 300 ml of ethanol and a few drops of water are added in order to dissolve the whole batch. The mixture is then evaporated under reduced pressure at 30°. An orange-yellow solid is obtained, which is dissolved in two liters of water, and the solution is acidified to pH ∝ 5 with citric acid. The pasty precipitate obtained is taken up in four liters of ether. The ether solution is dried and concentrated. An orange oil is thus obtained, which crystallises on trituration with petroleum ether. Recrystallisation from cyclohexane gives 4-N-[α-(4-fluorophenyl)-5-fluoro-2-hydroxy-benzylidenyl]-amino-butyric acid melting point=89.5°–90° in a yield of 52.5%.

The sodium salt of this acid is prepared in accordance with the method described in Example 1. It is obtained in a yield of 85.7%. It melts at 231° (with decomposition).

| Analysis: | | | | | |
|---|---|---|---|---|---|
| Calc. % (with 2.05% of water) | C 58.60 | H 4.29 | N 4.02 | F 10.90 | Na 6.60 |
| Found %: | 59.07 | 4.33 | 3.93 | 10.69 | — |
| | 58.97 | 4.27 | 3.93 | 10.87 | 6.28 |

The IR and NMR spectra have confirmed the structure of this compound.

EXAMPLE 4

2N-[α-(3-Chlorophenyl)-5-fluoro-2-hydroxy-benzylidenyl]-amino-acetamide [(I): $X_1=5$-F, $X_2=$N, $X_3=3$-Cl, $n=1$, R=NH$_2$: code number: Sl-D.039]

6.73 ml of 3.14 N sodium methylate (0.021 mol) and 200 ml of methanol are added to a stirred suspension of 2.34 g (0.021 mol) of glycinamide in 200 ml of methanol.

The mixture is stirred for 10 minutes and about 5 ml of water are added, after which stirring is continued until solution is complete. 5.5 g (0.022 mol) of 3'-chloro-5-fluoro-2-hydroxy-benzophenone are then introduced and the mixture is evaporated to dryness under reduced pressure.

The residue is taken up in 200 ml of ether and 200 ml of methanol and is again evaporated under reduced pressure. This operation is repeated several times. Finally, the 2N-[α-(3-chlorophenyl)-5-fluoro-2-hydroxy-benzylidenyl]-amino-acetamide is crystallised by trituration with petroleum ether. 4.1 g of the product are collected, representing a yield of 63.2%. The compound melts at 160°.

| Analysis | | | |
|---|---|---|---|
| Calc. % (with 0.22% of water) | C 58.61 | H 3.95 | N 9.11 |
| Found %: | 58.47 | 4.15 | 9.09 |
|  | 58.44 | 4.05 | — |

The IR and NMR spectra have confirmed the structure of the compound.

EXAMPLE 5

Sodium 11-N-(α-phenyl-2-hydroxy-benzylidenyl)-amino-undecamoate [(I): $X_1=X_2=X_3=H$: n=10; R=CNa: code number: SL-D.075]

Using the method described in Example 1, the following are obtained successively: 11-N-(α-phenyl-2-hydroxy-benzylidenyl)-amino-undecanoic acid, melting point=74.5°–75.5°, and its sodium salt, melting point 236°–240° (decomposition).

| Analysis: | | | | |
|---|---|---|---|---|
| Calculated %: | C 71.44 | N 7.49 | N 3.47 | Na 5.70 |
| Found %: | 71.75 | 7.37 | 3.29 | 5.65 |
|  | 71.57 | 7.55 | 3.48 | — |

The IR and NMR spectra have confirmed the structure of the compound.

EXAMPLE 6

4-[(4-Chlorophenyl)-5-fluoro-2-hydroxy-benzylidenyl]-amino-butyramide ($X_1$=5-F; $X_2$=H; $X_3$=4-Cl; n=3; R=$NH_2$; code number: SLE 002)

22.3 g (0.1375 mol) of 95% pure corbonyldiimidazole are added in portions, over the course of 10 minutes, to a solution, stirred at 0°, of 42 g (0.125 mol) of 4-[α-(4-chlorophenyl)-5-fluoro-2-hydroxy-benzylidenyl]-amino-butyric acid in 130 ml of anhydrous THF, and the mixture is stirred in the cold for 15 minutes and then at ambient temperature for 15 minutes. The solution obtained is added dropwise, whilst stirring, to 800 ml of liquid ammonia and the mixture is stirred until evaporation is complete.

The oily residue is taken up in 500 ml of chloroform and the solution is washed with water, an aqueous bicarbonate solution and again with water. It is dried over $MgSO_4$ in the presence of vegetable charcoal and filtered, and the filtrate is evaporated to dryness. An oil is obtained, which crystallises by trituration in petroleum ether. The product is washed onto a frit with petroleum ether, and is there washed with petroleum ether and suction-drained to the maximum extent. It is recrystallised from a 1:1 mixture of cyclohexane and toluene, with treatment with vegetable charcoal, and is dried in a heated vacuum desiccator at 60°.

Weight obtained: 28 g; yield: 67%; melting point=133°–135° (Tottoli).

| Analysis: | C | H | N | Cl | F |
|---|---|---|---|---|---|
| Calculated %: | 60.99 | 4.82 | 8.37 | 10.59 | 5.67 |
| Found %: | 60.91 | 4.83 | 8.36 | 10.84 | 5.74 |
|  | 60.97 | 4.78 | 8.26 | 10.73 | 5.76 |

Table I provides the formulae and characteristics of a certain number of other compounds of the general formula (I) prepared according to Examples 1 to 6 or of minor variants of the methods described therein. The analyses and spectra in all cases confirmed the structure of the products obtained.

TABLE I

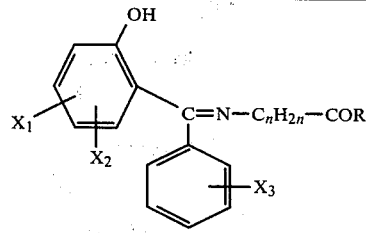

Examples 7 to 58

| Code number | $X_1$ | $X_2$ | $X_3$ | n | R | Characteristics |
|---|---|---|---|---|---|---|
| SL-C.227 | H | H | H | 3 | ONa | melting point = 218°<br>melting point of the acid = 128° |
| SL-D.005 | 5-Cl | H | H | 3 | ONa | melting point = 239–42° (decomposition)<br>melting point of the acid = 133–4° |
| SL-D.006 | H | H | H | 4 | ONa | melting point = 206°<br>melting point of the acid = 170–171° |
| SL-D.007 | H | H | H | 1 | ONa | melting point > 260° |
| SL-D.016 | 5-F | H | 3-Cl | 3 | ONa | melting point of the acid = 170°<br>melting point > 260° |
| SL-D.017 | 5-F | H | 2-F | 3 | ONa | melting point of the acid = 100°<br>melting point > 280°<br>melting point of the acid = 90° |

TABLE I-continued

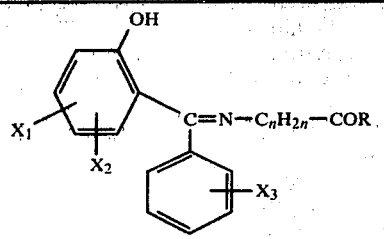

Examples 7 to 58

| Code number | X₁ | X₂ | X₃ | n | R | Characteristics |
|---|---|---|---|---|---|---|
| SL-D.019 | H | H | H | 2 | ONa | melting point = 240° (decomposition)<br>melting point of the acid = 185-6° |
| SL-D.026 | 3-CH₃ | H | H | 3 | ONa | melting point = 239-240°<br>melting point of the acid = 120° |
| SL-D.027 | 5-F | H | 2-Cl | 3 | ONa | melting point = 228-230°<br>the acid is an oil |
| SL-D.029 | 5-F | H | 2-CH₃ | 3 | ONa | melting point > 260° (decomposition) |
| SL-D.037 | H | H | H | 1 | NH₂ | melting point = 140° |
| SL-D.036 | 5-Cl | H | 2-F | 3 | ONa | melting point = 230° (decomposition)<br>melting point of the acid = 96° |
| SL-D.046 | H | H | 2-F | 3 | ONa | melting point = 178-9°<br>melting point of the acid = 96.5-97.5° |
| SL-D.053 | 5-CH₃ | H | 2-F | 3 | ONa | melting point > 260° (decomposition) |
| SL-D.054 | 5-F | H | H | 10 | ONa | melting point = 230° (decomposition)<br>melting point of the acid = 79° |
| SL-D.055 | 5-F | H | 3-F | 1 | NH₂ | melting point = 129.5-131° |
| SL-D.059 | 5-F | H | H | 5 | ONa | melting point = 236° (decomposition)<br>melting point of the acid = 129-130° |
| SL-D.074 | H | H | H | 5 | ONa | melting point = 210-12° (decomposition)<br>melting point of the acid = 123-4° |
| SL-D.078 | H | H | 2-Cl | 3 | ONa | melting point = 230°-5°<br>melting point of the acid = 93-94° |
| SL-D.083 | 5-F | H | H | 1 | NH₂ | melting point = 127-128° |
| SL-D.100 | H | H | H | 7 | ONa | melting point = 221-4° (decomposition)<br>melting point of the acid = 92-93° |
| SL-D.102 | 5-F | H | 4-Cl | 3 | ONa | melting point = 231-6° (decomposition)<br>melting point of the acid = 91.5-93° |
| SL-D.106 | 5-F | H | H | 4 | ONa | melting point = 300° (decomposition)<br>melting point of the acid = 178° |
| SL-D.107 | 4-OCH₃ | H | H | 3 | ONa | melting point = 200-200.5°<br>melting point of the acid = 134.5-135° |
| SL-D.118 | 4-OCH₃ | H | 4-Cl | 3 | ONa | melting point = 175-180° (decomposition)<br>melting point of the acid = 122-123° |
| SL-D.136 | 5-CH₃ | H | 2-Cl | 3 | ONa | melting point = 244-245° (decomposition)<br>melting point of the acid = 85-87° |
| SL-D.138 | 4-CH₃ | 5-Cl | H | 3 | ONa | melting point = 240-245° (decomposition)<br>melting point of the acid = 123.5-124° |
| SL-D.166 | 5-F | H | 4-F | 3 | NH₂ | melting point = 146.5-148° |
| SL-D.167 | 5-F | H | H | 3 | NH₂ | melting point = 144° |
| SL-D.168 | 5-F | H | H | 3 | —NH(CH₂)₃—COO<br>                    \|<br>                    C₂H₅ | melting point = 92° |
| SL-D.179 | 5-F | H | 4-F | 3 | —NH(CH₂)₃—COO<br>                    \|<br>                    C₂H₅ | melting point = 107-108° |
| SL-D.207 | 5-F | H | 4-F | 3 | —NH(CH₂)₃—COONa | melting point = 109-116°<br>melting point of the acid = 99-100.5° |
| SL-D.146 | 4-Br | H | H | 3 | —ONa | melting point = 220-227° (decomposition)<br>melting point of the acid 119-120.5° |
| SL-D.157 | 4-Cl | H | H | 3 | —ONa | melting point = 224-232° (decomposition)<br>melting point of the acid = 115.5-116.5° |
| SL-D.156 | 5-F | H | 3-CH₃ | 3 | —ONa | melting point > 260° (decomposition)<br>melting point of the acid = 107.5-108.5° |
| SLE - 002 | 5 F | H | 4 Cl | 3 | —NH₂ | melting point = 133-135° |
| SLE - 009 | 5 F | H | H | 3 | —NH—(cyclohexyl) | melting point = 154° |
| SLE - 010 | 5 F | H | H | 3 | —NH—(cyclopropyl) | melting point = 127° |

TABLE I-continued $$\underset{X_1}{\underset{X_2}{\bigodot}}\overset{OH}{\underset{\underset{X_3}{\bigodot}}{C}}=N-C_nH_{2n}-COR$$

Examples 7 to 58

| Code number | X₁ | X₂ | X₃ | n | R | Characteristics |
|---|---|---|---|---|---|---|
| SLE - 011 | 5 F | H | H | 3 | —NH—⬠ (cyclopentyl) | melting point = 124° |
| SLE - 012 | 5 F | H | H | 3 | —NH—C₆H₅ | melting point = 178° |
| SLE - 013 | 5 F | H | H | 3 | —NH—CH₂—C₆H₅ | melting point = 99° |
| SLE - 015 | 5 F | H | H | 3 | —N(H)(CH₃) | melting point = 114° |
| SLE - 022 | 5 F | H | H | 3 | —N(CH₃)₂ | melting point = 118° |
| SLE - 023 | 5 F | H | H | 3 | —N(nC₄H₉)₂ | melting point = 55-56° |
| SLE - 030 | 5 F | H | H | 3 | —NH—◇ (cyclopropyl) | melting point = 117° |
| SLE - 031 | 5 F | H | H | 3 | —NH—CH(CH₃)₂ | melting point = 136° |
| SLE - 085 | 5 F | H | H | 6  CnH2n = CH₂—CH₂—CH(CH₃CH₂CH₂)— | ONa | acid = 85-86° melting point = 237-240° (decomposition) |
| SLE - 086 | 5 F | H | 2 Cl | 3 | NH₂ | melting point = 110-111.5° |
| SLE - 091 | 5 F | H | 3 Cl | 3 | —NH₂ | melting point = 118-119° |
| SLE - 117 | 5 F | H | H | 3 | —NH—CH₂—C₆H₄—F | melting point = 106-107° |
| SLE 118 | 5 F | H | H | 3 | —N(CH₃)(CH₂C₆H₅) | liquid |
| SLE 134 | 3 F | H | H | 3 | —NH—CH₂—C₆H₄—CF₃ | melting point = 113.5-114.5° |

The compounds of the invention have been subjected to a series of pharmacological tests which have revealed their valuable properties.

I. Acute toxicity in mice

The compounds of the invention and the reference substances were administered intraperitoneally to CD₁ mice. The 50% lethal dose (LD 50) was determined graphically. The number of dead animals 48 hours after intraperitoneal administration was recorded. The results are summarised in Table II.

II. GABA-animetic activity of the compounds (I)

This activity is demonstrated by the antagonism to convulsions induced by bicuculline in mice. The experimental method of Curtis, D. R., et al., Brain Res., 1971, 33, 57 and Perez de la Mora, N., Biochem. Pharmacol., 1973, 22, 2,635, was used.

Bicuculline is a relatively selective blocking agent for GABA-sensitive post-synaptic receptors and its convulsive and lethal effects are antagonised by compounds which raise the cerebral concentration of GABA or possess a GABA-mimetic activity. The 50% active doses (AD 50), namely the doses which protect 50% of the animals against the effect of bicuculline, were evaluated for the substances studied. The results are presented in Table II.

The compounds of the invention, which are very active as anti-convulsants and of low toxicity, are therefore of great therapeutic interest in human and veterinary medicine in different types of epilepsy.

The invention consequently comprises pharmaceutical compositions which contain the compounds of formula (I) as active principles, in association with any compatible pharmaceutically acceptable excipients suitable for their administration, in particular their oral or parenteral administration. These pharmaceutical compositions can also contain other medicaments with which the compounds (I) are pharmacologically and therapeutically compatible.

For oral administration, any of the usual forms appropriate for this method of administration may be used, such as tablets, dragées, pills, capsules, cachets and potable solutions or suspensions, the unit weight of active principle being able to vary between 1 and 40 mg, and the daily posology between 5 and 400 mg.

For parenteral administration, sterile solutions prepared beforehand or at the time of use, and buffered to the physiological pH, are used. These solutions contain 0.5 to 10 mg of active principle in a volume of 1 to 5 ml. In practice, they are divided into ampoules containing from 1 to 5 ml, for administration by intramuscular or intravenous injection, or for administration by alow intravenous infusion. The daily dose for parenteral administration can be between 2 and 100 mg.

We claim:

1. A compound of the formula:

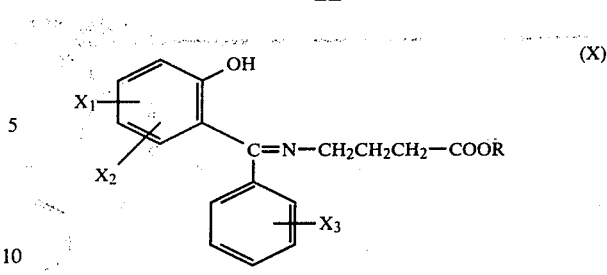

wherein,
each of $X_1$, $X_2$, and $X_3$ is independently hydrogen, halogen, methyl, or methoxy, and
R is hydrogen or an alkali metal atom.

2. A pharmaceutical composition for the treatment of epilepsy or convulsions in dosage unit form comprising a compound of the formula:

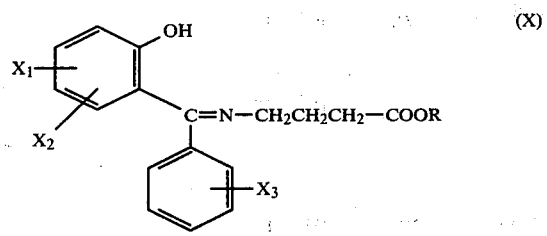

wherein,
each of $X_1$, $X_2$, and $X_3$ is independently hydrogen, halogen, methyl, or methoxy; and
R is hydrogen or an alkali metal atom;
said compound being present in an effective amount to relieve epilepsy or convulsions, and a pharmaceutically effective carrier therefor.

3. A method of relieving convulsions or epilepsy in a patient which comprises administering to said patient an anti-convulsively or anti-epileptically effective amount of a compound of the formula:

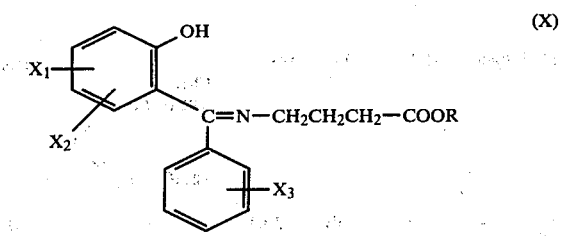

wherein,
each of $X_1$, $X_2$, and $X_3$ is independently hydrogen, halogen, methyl, or methoxy;
n is an integer from 1 to 10; and
R is hydrogen or an alkali metal atom;
except that when $X_1$, and $X_3$ are both hydrogen, n is 1, $X_2$ is not chlorine in the 5-position.

4. A pharmaceutical composition of claim 2, wherein said compound is 4-N-(α-phenyl-5-fluoro-2-hydroxy-benzylidenyl)-aminobutyric acid or a sodium salt thereof.

5. A pharmaceutical composition of claim 2, wherein said compound is 4-N-[α-(3-fluorophenyl)-5-fluoro-2-hydroxybenzylidenyl]-aminobutyric acid or a sodium salt thereof.

6. A pharmaceutical composition of claim 2, wherein said compound is 4-N-[α-(4-fluorophenyl)-5-fluoro-2-hydroxybenzylidenyl]-aminobutyric acid or a sodium salt thereof.

7. A compound of claim 1, which is 4-N-(α-phenyl-5-fluoro-2-hydroxy-benzylidenyl)-aminobutyric acid or a sodium salt thereof.

8. A compound of claim 1, which is 4-N-[α-(2-fluorophenyl)-5-fluoro-2-hydroxy-benzylidenyl]-aminobutyric acid or a sodium salt thereof.

9. A compound of claim 1, which is 4-N-[α-(4-fluorophenyl)-5-fluoro-2-hydroxy-benzylidenyl]-aminobutyric acid or a sodium salt thereof.

10. A method of claim 3, wherein said compound is 4-N-(α-phenyl-5-fluoro-2-hydroxy-benzylidenyl)-aminobutyric acid or a sodium salt thereof.

11. A method of claim 3, wherein said compound is 4-N-[α-(3-fluorophenyl)-5-fluoro-2-hydroxy-benzylidenyl]-aminobutyric acid or a sodium salt thereof.

12. A method of claim 3, wherein said compound is 4-N-[α-(4-fluorophenyl)-5-fluoro-2-hydroxy-benzylidenyl]-aminobutyric acid or a sodium salt thereof.

13. A pharmaceutical composition of claim 2 wherein said dosage unit form is for oral administration and selected from the group consisting of a tablet, dragee, pill, capsule, cachet, and a potable solution or suspension.

14. A pharmaceutical composition of claim 2 wherein said dosage unit form is for parenteral administration and is a sterile solution contained in an ampoule.

* * * * *

UNITED STATES PATENT AND TRADEMARK OFFICE
CERTIFICATE OF CORRECTION

PATENT NO.  : 4,400,394
DATED       : August 23, 1983
INVENTOR(S) : KAPLAN et al.

It is certified that error appears in the above-identified patent and that said Letters Patent is hereby corrected as shown below:

Table 1 at columns 7 and 8, change the $X_1$ substituent of compound SL-D.026 from "3-$CH_3$" to --5-$CH_3$--.

Table 1 at columns 9 and 10, change the R substituent of compound SLE-086 from "$MH_2$" to --$NH_2$--.

Signed and Sealed this

Sixth Day of November 1984

[SEAL]

*Attest:*

*Attesting Officer*

GERALD J. MOSSINGHOFF

*Commissioner of Patents and Trademarks*